United States Patent
Gao et al.

(10) Patent No.: US 8,252,955 B2
(45) Date of Patent: *Aug. 28, 2012

(54) TRIMERIZATION

(75) Inventors: Xiaoliang Gao, Calgary (CA); Charles Ashton Garret Carter, Calgary (CA); Lee Douglas Henderson, Calgary (CA)

(73) Assignee: NOVA Chemicals (International) S.A. (CH)

( * ) Notice: Subject to any disclaimer, the term of this patent is extended or adjusted under 35 U.S.C. 154(b) by 343 days.

This patent is subject to a terminal disclaimer.

(21) Appl. No.: 12/584,173

(22) Filed: Sep. 1, 2009

(65) Prior Publication Data

US 2010/0081842 A1   Apr. 1, 2010

(30) Foreign Application Priority Data

Sep. 29, 2008  (CA) ..................................... 2639870

(51) Int. Cl.
*C07F 9/02* (2006.01)
*C07C 2/10* (2006.01)

(52) U.S. Cl. .......... 564/12; 585/511; 585/514; 585/662; 585/659; 585/12

(58) Field of Classification Search ............ 564/12; 585/511, 514, 662, 659
See application file for complete search history.

(56) References Cited

U.S. PATENT DOCUMENTS

| | | | |
|---|---|---|---|
| 5,198,563 A | 3/1993 | Reagen et al. | |
| 5,340,785 A | 8/1994 | Reagen et al. | |
| 5,491,272 A | 2/1996 | Tanaka et al. | |
| 5,689,028 A | 11/1997 | Lashier et al. | |
| 5,750,817 A | 5/1998 | Tanaka et al. | |
| 5,856,257 A | 1/1999 | Freeman et al. | |
| 5,910,619 A | 6/1999 | Urata et al. | |
| 5,919,996 A | 7/1999 | Freeman et al. | |
| 6,800,702 B2 | 10/2004 | Wass | |
| 7,141,633 B2 * | 11/2006 | Wass | 526/124.3 |
| 7,525,009 B2 * | 4/2009 | Blann et al. | 585/527 |
| 7,829,749 B2 * | 11/2010 | Gao et al. | 585/527 |
| 7,906,681 B2 * | 3/2011 | Gao et al. | 564/12 |
| 2006/0173226 A1 | 8/2006 | Blann et al. | |
| 2006/0229480 A1 | 10/2006 | Blann et al. | |

OTHER PUBLICATIONS

Carter et al, High activity ethylene trimerisation catalysts based on diphosphine ligands, ChemComm, 2002, pp. 858-859.
Pangborn et al, Safe and Convenient Procedure for Solvent Purification, Organometallics, 1996, pp. 1518-1520, vol. 15, No. 5.

* cited by examiner

*Primary Examiner* — Peter G O Sullivan
(74) *Attorney, Agent, or Firm* — Kenneth H Johnson

(57) ABSTRACT

A new P—N—P ligand is useful in ethylene oligomerizations. In combination with i) a source of chromium and ii) an activator such as methylalumoxane; the ligand of this invention may be used to prepare an oligomer product that contains a mixture of hexenes and octenes. The hexenes and octenes produced with this ligand contain very low levels of internal olefins when produced under preferred reaction conditions.

12 Claims, No Drawings

TRIMERIZATION

FIELD OF THE INVENTION

This invention provides a new family of P—N—P ligands. The ligands are useful in ethylene oligomerization reactions.

BACKGROUND OF THE INVENTION

Alpha olefins are commercially produced by the oligomerization of ethylene in the presence of a simple alkyl aluminum catalyst (in the so called "chain growth" process) or alternatively, in the presence of an organometallic nickel catalyst (in the so called Shell Higher Olefins, or "SHOP" process). Both of these processes typically produce a crude oligomer product having a broad distribution of alpha olefins with an even number of carbon atoms (i.e. butene-1, hexene-1, octene-1 etc.). The various alpha olefins in the crude oligomer product are then typically separated in a series of distillation columns. Butene-1 is generally the least valuable of these olefins as it is also produced in large quantities as a by-product in various cracking and refining processes. Hexene-1 and octene-1 often command comparatively high prices because these olefins are in high demand as comonomers for linear low density polyethylene (LLDPE).

Technology for the selective trimerization of ethylene to hexene-1 has been recently put into commercial use in response to the demand for hexene-1. The patent literature discloses catalysts which comprise a chromium source and a pyrrolide ligand as being useful for this process—see, for example, U.S. Pat. No. 5,198,563 (Reagen et al., assigned to Phillips Petroleum).

Another family of highly active trimerization catalysts is disclosed by Wass et al. in WO 02/04119 (now U.S. Pat. Nos. 7,143,633 and 6,800,702. The catalysts disclosed by Wass et al. are formed from a chromium source and a chelating diphosphine ligand and are described in further detail by Carter et al. (Chem. Comm. 2002, p 858-9). As described in the Chem. Comm. paper, these catalysts preferably comprise a diphosphine ligand in which both phosphine atoms are bonded to two phenyl groups that are each substituted with an ortho-methoxy group. Hexene-1 is produced with high activity and high selectivity by these catalysts.

Similar diphosphine/tetraphenyl ligands are disclosed by Blann et al. in WO04/056478 and WO 04/056479 (now US 2006/0229480 and US 2006/0173226). However, in comparison to the ligands of Wass et al., the disphosphine/tetraphenyl ligands disclosed by Blann et al. generally do not contain polar substituents in ortho positions. The "tetraphenyl" diphosphine ligands claimed in the '480 application must not have ortho substituents (of any kind) on all four of the phenyl groups and the "tetraphenyl" diphosphine ligands claimed in '226 are characterized by having a polar substituent in a meta or para position. Both of these approaches are shown to reduce the amount of hexenes produced and increase the amount of octene (in comparison to the ligands of Wass et al.). However, the hexene fraction generally contains a large portion of internal hexenes, which is undesirable. Thus, chromium based catalysts which contain the ligands of Blann et al. typically produce more octene (which may be advantageous if demand for octene is high) but these ligands have the disadvantage of producing a hexene stream which is contaminated with a comparatively large amount of internal olefins.

Internal olefins are undesirable contaminants in linear low density polyethylene (LLDPE) production facilities because the internal olefins are not readily incorporated into LLDPE with most transition metal catalysts. Thus, it is preferable to remove/separate internal olefins from alpha olefins if the alpha olefin is to be used in an LLDPE process. As will be appreciated by those skilled in the art, it is comparatively difficult to separate hexene-1 from internal hexenes by distillation due to the close boiling points of these hexene isomers.

Accordingly, a process which selectively produces a mixture of hexene-1 and octene-1 with very low levels of internal olefins represents a desirable addition to the art.

SUMMARY OF THE INVENTION

In one embodiment, the present invention provides a new family of P—N—P ligands defined by the formula:

wherein each of $Ph_1$, $Ph_2$, $Ph_3$ and $Ph_4$ is a phenyl group bonded to a phosphorus atom, with the provisos that
 i) at least one of $Ph_1$, $Ph_2$, $Ph_3$ and $Ph_4$ is ortho substituted with a halogen selected from the group consisting of fluorine, bromine and chlorine;
 ii) at least one of $Ph_1$, $Ph_2$, $Ph_3$ and $Ph_4$ is ortho substituted with a polar substituent; and
 iii) $R_2$ is selected from the group consisting of hydrogen, $C_{1-20}$ hydrocarbyl and silyl.

These molecules are particularly suitable for use as a ligand in a process to oligomerize ethylene. Potential alternative uses include ligands for hydrogenation and/or hydroformylation reactions.

Attempts to produce the new ligands by conventional condensation reactions (i.e., using a precursor amine and a precursor diphosphine chloride) were unsuccessful. Accordingly, another embodiment of this invention provides a new synthetic route to this family of molecules. A preferred synthesis is described in more detail in the Examples.

Another embodiment of this invention provides a catalyst system comprising:
 a) a transition metal selected from the group consisting of Cr, V, Ti, Ni, and W;
 b) A ligand defined by the formula:

wherein each of $Ph_1$, $Ph_2$, $Ph_3$ and $Ph_4$ is a phenyl group bonded to a phosphorus atom, with the provisos that
  i) at least one of $Ph_1$, $Ph_2$, $Ph_3$ and $Ph_4$ is ortho substituted with a halogen selected from the group consisting of fluorine, bromine and chlorine;
  ii) at least one of $Ph_1$, $Ph_2$, $Ph_3$ and $Ph_4$ is ortho substituted with a polar substituent; and
  iii) $R_2$ is selected from the group consisting of hydrogen, $C_{1-20}$ hydrocarbyl and silyl; and
 c) an activator.

The oligomerization process of this invention may be conducted under conventional oligomerization conditions. One important advantage of the present invention is that the product olefins can comprise a desirable mixture of hexene and octene (in particular, greater than 80 weight % of the ethylene that is converted to a liquid product during the process can be hexenes and octenes) with very low levels of internal olefins (preferably less than 15 weight % of the mixed hexene and octene stream is internal olefins) when the process is conducted under preferred temperature and pressure conditions.

DETAILED DESCRIPTION OF PREFERRED EMBODIMENTS

Part A: Catalyst System

The catalyst system used in the process of the present invention must contain three essential components, namely:
(i) a source of chromium:
(ii) a defined P—N—P ligand; and
(iii) an activator.
Preferred forms of each of these components are discussed below.

Chromium Source ("Component (i)")

Any source of chromium which allows the oligomerization process of the present invention to proceed may be used. Preferred chromium sources include chromium trichloride; chromium (III) 2-ethylhexanoate; chromium (III) acetylacetonate and chromium carboxyl complexes such as chromium hexacarboxyl.

Ligand Used in the Oligomerization Process ("Component (ii)")

In general, the ligand used in the oligomerization process of this invention is defined by the formula:

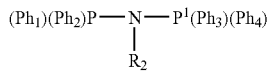

wherein each of $Ph_1$, $Ph_2$, $Ph_3$ and $Ph_4$ is a phenyl group bonded to a phosphorus atom, with the provisos that
i) at least one of $Ph_1$, $Ph_2$, $Ph_3$ and $Ph_4$ is ortho substituted with a halogen selected from the group consisting of fluorine, bromine and chlorine;
ii) at least one of $Ph_1$, $Ph_2$, $Ph_3$ and $Ph_4$ is ortho substituted with a polar substituent; and
iii) $R_2$ is selected from the group consisting of hydrogen, $C_{1-20}$ hydrocarbyl and silyl.

Each halogen is preferably fluorine.

$R_2$ is preferably a hydrocarbyl group having from 1 to 20 carbon atoms. The analogous silyl groups may also be employed. The hydrocarbyl groups of $R_2$ may contain heteroatom substituents (having a heteroatom selected from O, N, P and S). Simple alkyl groups having from 1 to 12 carbon atoms are preferred. Isopropyl is particularly preferred.

As used herein, the term "polar" refers to a substituent with a dipole moment. Examples include $C_{1-20}$ alkoxy (with methoxy, ethoxy and isopropoxy being preferred—especially methoxy); phenoxy, hydroxyl, amino, sulfate and the like. Alkoxy substituents are most preferred, especially methoxy.

In a preferred embodiment, the substituents on the four phenyl groups satisfy another condition, namely that all of $Ph_1$, $Ph_2$, $Ph_3$ and $Ph_4$ are either ortho substituted with a halogen (preferably fluorine) or ortho substituted with a polar substituent (especially an alkoxy substituent).

The ortho substituents on the phenyl groups of the present ligands are critical to the present invention. Substituents at meta or para positions are generally less important but are contemplated within the scope of the present invention.

Activator ("Component (iii)")

The activator (component (iii)) may be any compound that generates an active catalyst for ethylene oligomerization with components (i) and (ii). Mixtures of activators may also be used. Suitable compounds include organoaluminum compounds, organoboron compounds and inorganic acids and salts, such as tetrafluoroboric acid etherate, silver tetrafluoroborate, sodium hexafluoroantimonate and the like. Suitable organoaluminum compounds include compounds of the formula $AlR_3$, where each R is independently $C_1$-$C_{12}$ alkyl, oxygen or halide, and compounds such as $LiAlH_4$ and the like. Examples include trimethylaluminum (TMA), triethylaluminum (TEA), tri-isobutylaluminium (TIBA), tri-n-octylaluminium, methylaluminium dichloride, ethylaluminium dichloride, dimethylaluminium chloride, diethylaluminium chloride, ethylaluminiumsesquichloride, methylaluminiumsesquichloride, and alumoxanes. Alumoxanes are well known in the art as typically oligomeric compounds which can be prepared by the controlled addition of water to an alkylaluminium compound, for example trimethylaluminium. Such compounds can be linear, cyclic, cages or mixtures thereof. Commercially available alumoxanes are generally believed to be mixtures of linear and cyclic compounds. The cyclic alumoxanes can be represented by the formula $[R^6AlO]_s$ and the linear alumoxanes by the formula $R^7(R^8AlO)_s$ wherein s is a number from about 2 to 50, and wherein $R^6$, $R^7$, and $R^8$ represent hydrocarbyl groups, preferably $C_1$ to $C_6$ alkyl groups, for example methyl, ethyl or butyl groups. Alkylalumoxanes especially methylalumoxane (MAO) are preferred. (MAO is also referred to as methalumoxane and methylaluminoxane in the literature).

It will be recognized by those skilled in the art that commercially available alkylalumoxanes may contain a proportion of trialkylaluminium. For instance, commercial MAO usually contains approximately 10 wt % trimethylaluminium (TMA), and commercial "modified MAO" (or "MMAO") contains both TMA and TIBA. Quantities of alkylalumoxane are generally quoted herein on a molar basis of aluminium (and include such "free" trialkylaluminium). The alkylalumoxane and/or alkylaluminium may be added to the reaction media (i.e. ethylene and/or diluent and/or solvent) prior to the addition of the catalyst or at the same time as the catalyst is added. Such techniques are known in the art of oligomerization and are disclosed in more detail in for example, U.S. Pat. Nos. 5,491,272; 5,750,817; 5,856,257; 5,910,619; and 5,919,996.

Examples of suitable organoboron compounds are boroxines, $NaBH_4$, trimethylboron, triethylboron, dimethylphenylammoniumtetra(phenyl)borate, trityltetra(phenyl)borate, triphenylboron, dimethylphenylammonium tetra(pentafluorophenyl)borate, sodium tetrakis[(bis-3,5-trifluoromethyl)phenyl]borate, trityltetra(pentafluorophenyl)borate and tris (pentafluorophenyl) boron.

Activator compound (iii) may also be or contain a compound that acts as a reducing or oxidizing agent, such as sodium or zinc metal and the like, or oxygen and the like.

In the preparation of the catalyst systems used in the present invention, the quantity of activating compound to be employed is easily determined by simple testing, for example, by the preparation of small test samples which can be used to oligimerize small quantities of ethylene and thus to determine the activity of the produced catalyst. It is generally found that the quantity employed is sufficient to provide 0.5 to 1000 moles of aluminium (or boron) per mole of chromium. MAO is the presently preferred activator. Molar Al/Cr ratios of from 1/1 to 500/1 are preferred.

Part B: Process Conditions

The chromium (component (i)) and ligand (component (ii)) may be present in any molar ratio which produces oligomer, preferably between 100:1 and 1:100, and most preferably from 10:1 to 1:10, particularly 3:1 to 1:3. Generally the amounts of (i) and (ii) are approximately equal, i.e. a ratio of between 1.5:1 and 1:1.5.

Components (i)-(iii) of the catalyst system utilized in the present invention may be added together simultaneously or sequentially, in any order, and in the presence or absence of ethylene in any suitable solvent, so as to give an active catalyst. For example, components (i), (ii) and (iii) and ethylene may be contacted together simultaneously, or components (i), (ii) and (iii) may be added together simultaneously or sequentially in any order and then contacted with ethylene, or components (i) and (ii) may be added together to form an isolable metal-ligand complex and then added to component (iii) and contacted with ethylene, or components (i), (ii) and (iii) may be added together to form an isolable metal-ligand complex and then contacted with ethylene. Suitable solvents for contacting the components of the catalyst or catalyst system include, but are not limited to, hydrocarbon solvents such as heptane, toluene, 1-hexene and the like, and polar solvents such as diethyl ether, tetrahydrofuran, acetonitrile, dichloromethane, chloroform, chlorobenzene, methanol, acetone and the like.

The catalyst components (i), (ii) and (iii) utilized in the present invention can be unsupported or supported on a support material, for example, silica, alumina, $MgCl_2$ or zirconia, or on a polymer, for example polyethylene, polypropylene, polystyrene, or poly(aminostyrene). If desired the catalysts can be formed in situ in the presence of the support material, or the support material can be pre-impregnated or premixed, simultaneously or sequentially, with one or more of the catalyst components. The quantity of support material employed can vary widely, for example from 100,000 to 1 grams per gram of metal present in the transition metal compound. In some cases, the support material can also act as or as a component of the activator compound (iii). Examples include supports containing alumoxane moieties.

The oligomerization can be, conducted under solution phase, slurry phase, gas phase or bulk phase conditions. Suitable temperatures range from 10° C. to +300° C. preferably from 10° C. to 100° C., especially from 40° C. to 80° C. Suitable pressures are from atmospheric to 800 atmospheres (gauge) preferably from 5 atmospheres to 100 atmospheres, especially from 10 to 50 atmospheres.

Irrespective of the process conditions employed, the oligomerization is typically carried out under conditions that substantially exclude oxygen, water, and other materials that act as catalyst poisons. Also, oligomerization can be carried out in the presence of additives to control selectivity, enhance activity and reduce the amount of polymer formed in oligomerization processes. Potentially suitable additives include, but are not limited to, hydrogen or a halide source.

There exist a number of options for the oligomerization reactor including batch, semi-batch, and continuous operation. The reactions of the present invention can be performed under a range of process conditions that are readily apparent to those skilled in the art: as a homogeneous liquid phase reaction in the presence or absence of an inert hydrocarbon diluent such as toluene or heptanes; as a two-phase liquid/liquid reaction; as a slurry process where the catalyst is in a form that displays little or no solubility; as a bulk process in which essentially neat reactant and/or product olefins serve as the dominant medium; as a gas-phase process in which at least a portion of the reactant or product olefin(s) are transported to or from a supported form of the catalyst via the gaseous state. Evaporative cooling from one or more monomers or inert volatile liquids is but one method that can be employed to effect the removal of heat from the reaction. The reactions may be performed in the known types of gas-phase reactors, such as circulating bed, vertically or horizontally stirred-bed, fixed-bed, or fluidized-bed reactors, liquid-phase reactors, such as plug-flow, continuously stirred tank, or loop reactors, or combinations thereof. A wide range of methods for effecting product, reactant, and catalyst separation and/or purification are known to those skilled in the art and may be employed: distillation, filtration, liquid-liquid separation, slurry settling, extraction, etc. One or more of these methods may be performed separately from the oligomerization reaction or it may be advantageous to integrate at least some with the reaction; a non-limiting example of this would be a process employing catalytic (or reactive) distillation. Also advantageous may be a process which includes more than one reactor, a catalyst kill system between reactors or after the final reactor, or an integrated reactor/separator/purifier. While all catalyst components, reactants, inerts and products could be employed in the present invention on a once-through basis, it is often economically advantageous to recycle one or more of these materials; in the case of the catalyst system, this might require reconstituting one or more of the catalysts components to achieve the active catalyst system. It is within the scope of this invention that an oligomerization product might also serve as a solvent or diluent. Mixtures of inert diluents or solvents also could be employed. The preferred diluents or solvents are aliphatic and aromatic hydrocarbons and halogenated hydrocarbons such as, for example, isobutane, pentane, toluene, xylene, ethylbenzene, cumene, mesitylene, heptane, cyclohexene, methylcyclohexene, 1-hexene, 1-octene, chlorobenzene, dichlorobenzene, and the like, and mixtures such as Isopar™.

Techniques for varying the distribution of products from the oligomerization reactions include controlling process conditions (e.g. concentration of components (i)-(iii), reaction temperature, pressure, residence time) and properly selecting the design of the process and are well known to those skilled in the art.

The ethylene feedstock for the oligomerization may be substantially pure or may contain other olefinic impurities and/or ethane. One embodiment of the process of the invention comprises the oligomerization of ethylene-containing waste streams from other chemical processes or a crude ethylene/ethane mixture from a cracker.

It is also within the scope of the present invention to conduct an oligomerization reaction in the presence of two or more oligomerization catalysts. In one embodiment, all of the oligomerization catalysts may be prepared with variants of the present novel P—N—P ligands. In another embodiment, a different form of oligomerization catalyst may be used in combination with a catalyst prepared from the present P—N—P ligands.

In a highly preferred embodiment of the present invention, the oligomerization product produced from this invention is added to a product stream from another alpha olefins manufacturing process for separation into different alpha olefins. As previously discussed, "conventional alpha olefin plants" (wherein the term includes i) those processes which produce alpha olefins by a chain growth process using an aluminum alkyl catalyst, ii) the aforementioned "SHOP" process and iii) the production of olefins from synthesis gas using the so called Lurgi process) have a series of distillation columns to separate the "crude alpha product" (i.e. a mixture of alpha olefins) into alpha olefins (such as butene-1, hexene-1 and octene-1). The mixed hexene-octene product which is produced in accordance with the present invention is highly suitable for addition/mixing with a crude alpha olefin product from an existing alpha olefin plant (or a "cut" or fraction of the product from such a plant) because the mixed hexene-octene product produced in accordance with the present invention can have very low levels of internal olefins. Thus, the hexene-octene product of the present invention can be readily separated in the existing distillation columns of alpha olefin plants (without causing the large burden on the operation of these distillation columns which would otherwise exist if the present hexene-octene product stream contained large quantities of internal olefins). As used herein, the term "liquid product" is meant to refer to the oligomers produced by the process of the present invention which have from 4 to (about) 20 carbon atoms.

The liquid product from the oligomerization process of the present invention preferably consists of from 50 to 90 weight % linear hexenes (especially from 35 to 75 weight %) where all of the weight % is expressed on the basis of the weight of liquid product. In view of the large amount of hexene produced, the oligomerization reaction of this invention may be referred to as a "trimerization".

The preferred oligomerization process of this invention is also characterized by producing very low levels of internal olefins (i.e. low levels of hexene-2, hexene-3, octene-2, octene-3 etc.), with preferred levels of less than 10 weight % (especially less than 5 weight %) of the hexenes and octenes being internal olefins. Low levels of internal hexenes (e.g. hexene-2 and/or hexene-3) are highly desirable because:

a) internal hexenes generally have boiling points that are very close to the boiling point of hexene-1 (and hence are difficult to separate from hexene-1 by distillation); and b) internal hexenes are difficult to copolymerize with ethylene using conventional catalysts (in comparison to hexene-1) and hence are not desired for use in most copolymerizations.

It is generally preferred to deactivate the oligomerization catalyst at the end of the polymerization reaction. In general, many polar compounds (such as water, alcohols and carboxcylic acids) will deactivate the catalyst. The use of alcohols and/or carboxcylic acids is preferred—and combinations of both are contemplated.

It is also preferred to remove the catalyst (and by-product polymer, if any) from the liquid product stream. Techniques for catalyst deactivation/product recovery that are known for use with other oligomerization catalysts should also be generally suitable for use with the present catalysts (see for example, U.S. Pat. Nos. 5,689,208 and 5,340,785.

One embodiment of the present invention encompasses the use of components (i) (ii) and (iii) in conjunction with one or more types of olefin polymerization catalyst system (iv) to trimerise ethylene and subsequently incorporate a portion of the trimerisation product(s) into a higher polymer.

Component (iv) may be one or more suitable polymerization catalyst system(s), examples of which include, but are not limited to, conventional Ziegler-Natta catalysts, metallocene catalysts, monocyclopentadienyl or "constrained geometry" catalysts, phosphinimine catalysts, heat activated supported chromium oxide catalysts (e.g. "Phillips"-type catalysts), late transition metal polymerization catalysts (e.g. diimine, diphosphine and salicylaldimine nickel/palladium catalysts, iron and cobalt pyridyldiimine catalysts and the like) and other so-called "single site catalysts" (SSC's).

Ziegler-Natta catalysts, in general, consist of two main components. One component is an alkyl or hydride of a Group I to III metal, most commonly $Al(Et)_3$ or $Al(iBu)_3$ or $Al(Et)_2Cl$ but also encompassing Grignard reagents, n-butyllithium, or dialkylzinc compounds. The second component is a salt of a Group IV to VIII transition metal, most commonly halides of titanium or vanadium such as $TiCl_4$, $TiCl_3$, $VCl_4$, or $VOCl_3$. The catalyst components when mixed, usually in a hydrocarbon solvent, may form a homogeneous or heterogeneous product. Such catalysts may be impregnated on a support, if desired, by means known to those skilled in the art and so used in any of the major processes known for co-ordination catalysis of polyolefins such as solution, slurry, and gas-phase. In addition to the two major components described above, amounts of other compounds (typically electron donors) maybe added to further modify the polymerization behaviour or activity of the catalyst.

Metallocene catalysts, in general, consist of transition metal complexes, most commonly based on Group IV metals, ligated with cyclopentadienyl(Cp)-type groups. A wide range of structures of this type of catalysts is known, including those with substituted, linked and/or heteroatom-containing Cp groups, Cp groups fused to other ring systems and the like. Additional activators, such as boranes or alumoxane, are often used and the catalysts may be supported, if desired.

Monocyclopentadienyl or "constrained geometry" catalysts, in general, consist of a transition metal complexes, most commonly based on Group IV metals, ligated with one cyclopentadienyl(Cp)-type group, often linked to additional donor group. A wide range of structures of this type of catalyst is known, including those with substituted, linked and/or heteroatom-containing Cp groups, Cp groups fused to other ring systems and a range of linked and non-linked additional donor groups such as amides, amines and alkoxides. Additional activators, such as boranes or alumoxane, are often used and the catalysts may be supported, if desired.

A typical heat activated chromium oxide (Phillips) type catalyst employs a combination of a support material to which has first been added a chromium-containing material wherein at least part of the chromium is in the hexavalent state by heating in the presence of molecular oxygen. The support is generally composed of about 80 to 100 wt. % silica, the remainder, if any, being selected from the group consisting of refractory metal oxides, such as aluminium, boria, magnesia, thoria, zirconia, titania and mixtures of two or more of these refractory metal oxides. Supports can also comprise alumina, aluminium phosphate, boron phosphate and mixtures thereof with each other or with silica. The chromium compound is typically added to the support as a chromium (III) compound such as the acetate or acetylacetonate in order to avoid the toxicity of chromium (VI). The raw catalyst is then calcined in air at a temperature between 250 and 1000° C. for a period of from a few seconds to several hours. This converts at least part of the chromium to the hexavalent state. Reduction of the Cr (VI) to its active form normally occurs in the polymerization reaction, but can be done at the end of the calcination cycle with CO at about 350° C. Additional compounds, such as fluorine, aluminium and/or titanium may be added to the raw Phillips catalyst to modify it.

Late transition metal and single site catalysts cover a wide range of catalyst structures based on metals across the transition series.

Component (iv) may also comprise one or more polymerization catalysts or catalyst systems together with one or more additional oligomerization catalysts or catalyst systems. Suitable oligomerization catalysts include, but are not limited to, those that dimerise (for example, nickel phosphine dimerisation catalysts) or trimerise olefins or otherwise oligomerize olefins to, for example, a broader distribution of 1-olefins (for example, iron and cobalt pyridyldiimine oligomerization catalysts).

Component (iv) may independently be supported or unsupported. Where components (i) and (ii) and optionally (iii) are supported, (iv) may be co-supported sequentially in any order or simultaneously on the same support or may be on a separate support. For some combinations, the components (i) (iii) may be part or all of component (iv). For example, if component (iv) is a heat activated chromium oxide catalyst then this may be (i), a chromium source and if component (iv) contains an alumoxane activator then this may also be the optional activator (iii).

The components (i), (ii), (iii) and (iv) may be in essentially any molar ratio that produces a polymer product. The precise ratio required depends on the relative reactivity of the components and also on the desired properties of the product or catalyst systems.

An "in series" process could be conducted by first conducting the oligomerization reaction, then passing the oligomerization product to a polymerization reaction. In the case of an "in series" process various purification, analysis and control steps for the oligomeric product could potentially be incorporated between the trimerization and subsequent reaction stages. Recycling between reactors configured in series is also possible. An example of such a process would be the oligomerization of ethylene in a single reactor with a catalyst comprising components (i)-(iii) followed by co-polymerization of the oligomerization product with ethylene in a separate, linked reactor to give branched polyethylene. Another example would be the oligomerization of an ethylene-containing waste stream from a polyethylene process, followed by introduction of the oligomerization product back into the polyethylene process as a co-monomer for the production of branched polyethylene.

An example of an "in situ" process is the production of branched polyethylene catalyzed by components (i)-(iv), added in any order such that the active catalytic species derived from components (i)-(iii) are at some point present in a reactor with component (iv).

Both the "in series" and "in situ" approaches can be adaptions of current polymerization technology for the process stages including component (iv). All major olefin existing polymerization processes, including multiple reactor processes, are considered adaptable to this approach. One adaption is the incorporation of an oligomerization catalyst bed into a recycle loop of a gas phase polymerization process, this could be as a side or recycle stream within the main fluidization recycle loop and or within the degassing recovery and recycle system.

Polymerization conditions when component (iv) is present can be, for example, solution phase, slurry phase, gas phase or bulk phase, with temperatures ranging from $-100°$ C. to $+300°$ C., and at pressures of atmospheric and above, particularly from 1.5 to 50 atmospheres. Reaction conditions, will typically have a significant impact upon the properties (e.g. density, melt index, yield) of the polymer being made and it is likely that the polymer requirements will dictate many of the reaction variables. Reaction temperature, particularly in processes where it is important to operate below the sintering temperature of the polymer, will typically, and preferably, be primarily selected to optimize the polymerization reaction conditions. Also, polymerization or copolymerization can be carried out in the presence of additives to control polymer or copolymer molecular weights. The use of hydrogen gas as a means of controlling the average molecular weight of the polymer or copolymer applies generally to the polymerization process of the present invention.

Slurry phase polymerization conditions or gas phase polymerization conditions are particularly useful for the production of high or low density grades of polyethylene, and polypropylene. In these processes the polymerization conditions can be batch, continuous or semi-continuous. Furthermore, one or more reactors may be used, e.g. from two to five reactors in series. Different reaction conditions, such as different temperatures or hydrogen concentrations may be employed in the different reactors.

Once the polymer product is discharged from the reactor, any associated and absorbed hydrocarbons are substantially removed, or degassed, from the polymer by, for example, pressure let-down or gas purging using fresh or recycled steam, nitrogen or light hydrocarbons (such as ethylene). Recovered gaseous or liquid hydrocarbons may be recycled to a purification system or the polymerization zone.

In the slurry phase polymerization process the polymerization diluent is compatible with the polymer(s) and catalysts, and may be an alkane such as hexene, heptane, isobutane, or a mixture of hydrocarbons or paraffins. The polymerization zone can be, for example, an autoclave or similar reaction vessel, or a continuous liquid full loop reactor, e.g. of the type well-known in the manufacture of polyethylene by the Phillips Process. When the polymerization process of the present invention is carried out under slurry conditions the polymerization is preferably carried out at a temperature above $0°$ C., most preferably above $15°$ C. Under slurry conditions the polymerization temperature is preferably maintained below the temperature at which the polymer commences to soften or sinter in the presence of the polymerization diluent. If the temperature is allowed to go above the latter temperature, fouling of the reactor can occur. Adjustment of the polymerization within these defined temperature ranges can provide a useful means of controlling the average molecular weight of the produced polymer. A further useful means of controlling the molecular weight is to conduct the polymerization in the presence of hydrogen gas which acts as chain transfer agent. Generally, the higher the concentration of hydrogen employed, the lower the average molecular weight of the produced polymer.

In bulk polymerization processes, liquid monomer such as propylene is used as the polymerization medium.

Methods for operating gas phase polymerization processes are well known in the art. Such methods generally involve agitating (e.g. by stirring, vibrating or fluidizing) a bed of catalyst, or a bed of the target polymer (i.e. polymer having the same or similar physical properties to that which it is desired to make in the polymerization process) containing a catalyst, and feeding thereto a stream of monomer (under conditions such that at least part of the monomer polymerizes in contact with the catalyst in the bed. The bed is generally cooled by the addition of cool gas (e.g. recycled gaseous monomer) and/or volatile liquid (e.g. a volatile inert hydrocarbon, or gaseous monomer which has been condensed to form a liquid). The polymer produced in, and isolated from, gas phase processes forms directly a solid in the polymerization zone and is free from, or substantially free from liquid. As is well known to those skilled in the art, if any liquid is allowed to enter the polymerization zone of a gas phase polymerization process the quantity of liquid in the polymerization zone is small in relation to the quantity of polymer present. This is in contrast to "solution phase" processes wherein the polymer is formed dissolved in a solvent, and "slurry phase" processes wherein the polymer forms as a suspension in a liquid diluent.

The gas phase process can be operated under batch, semi-batch, or so-called "continuous" conditions. It is preferred to operate under conditions such that monomer is continuously recycled to an agitated polymerization zone containing polymerization catalyst, make-up monomer being provided to replace polymerized monomer, and continuously or intermittently withdrawing produced polymer from the polymerization zone at a rate comparable to the rate of formation of the polymer, fresh catalyst being added to the polymerization zone to replace the catalyst withdrawn from the polymerization zone with the produced polymer.

Methods for operating gas phase fluidized bed processes for making polyethylene, ethylene copolymers and polypropylene are well known in the art. The process can be operated, for example, in a vertical cylindrical reactor equipped with a perforated distribution plate to support the bed and to distribute the incoming fluidizing gas stream through the bed. The fluidizing gas circulating through the bed serves to remove the heat of polymerization from the bed and to supply monomer for polymerization in the bed. Thus the fluidizing gas generally comprises the monomer(s) normally together with some inert gas (e.g. nitrogen or inert hydrocarbons such as methane, ethane, propane, butane, pentane or hexene) and optionally with hydrogen as molecular weight modifier. The hot fluidizing gas emerging from the top of the bed is led optionally through a velocity reduction zone (this can be a cylindrical portion of the reactor having a wider diameter) and, if desired, a cyclone and or filters to disentrain fine solid particles from the gas stream. The hot gas is then led to a heat exchanger to remove at least part of the heat of polymerization. Catalysts are preferably fed continuously or at regular intervals to the bed. At start up of the process, the bed comprises fluidizable polymer which is preferably similar to the target polymer. Polymer is produced continuously within the bed by the polymerization of the monomer(s). Preferably means are provided to discharge polymer from the bed continuously or at regular intervals to maintain the fluidized bed at the desired height. The process is generally operated at relatively low pressure, for example, at 10 to 50 atmospheres, and at temperatures for example, between 50 and 135° C. The temperature of the bed is maintained below the sintering temperature of the fluidized polymer to avoid problems of agglomeration.

In the gas phase fluidized bed process for polymerization of olefins the heat evolved by the exothermic polymerization reaction is normally removed from the polymerization zone (i.e. the fluidized bed) by means of the fluidizing gas stream as described above. The hot reactor gas emerging from the top of the bed is led through one or more heat exchangers wherein the gas is cooled. The cooled reactor gas, together with any make-up gas, is then recycled to the base of the bed. In the gas phase fluidized bed polymerization process of the present invention it is desirable to provide additional cooling of the bed (and thereby improve the space time yield of the process) by feeding a volatile liquid to the bed under conditions such that the liquid evaporates in the bed thereby absorbing additional heat of polymerization from the bed by the "latent heat of evaporation" effect. When the hot recycle gas from the bed enters the heat exchanger, the volatile liquid can condense out. In one embodiment of the present invention the volatile liquid is separated from the recycle gas and reintroduced separately into the bed. Thus, for example, the volatile liquid can be separated and sprayed into the bed. In another embodiment of the present invention the volatile liquid is recycled to the bed with the recycle gas. Thus the volatile liquid can be condensed from the fluidizing gas stream emerging from the reactor and can be recycled to the bed with recycle gas, or can be separated from the recycle gas and then returned to the bed.

A number of process options can be envisaged when using the catalysts of the present invention in an integrated process to prepare higher polymers i.e. when component (iv) is present. These options include "in series" processes in which the oligomerization and subsequent polymerization are carried in separate but linked reactors and "in situ" processes in which a both reaction steps are carried out in the same reactor.

In the case of a gas phase "in situ" polymerization process, component (iv) can, for example, be introduced into the polymerization reaction zone in liquid form, for example, as a solution in a substantially inert liquid diluent. Components (i)-(iv) may be independently added to any part of the polymerization reactor simultaneously or sequentially together or separately. Under these circumstances it is preferred the liquid containing the component(s) is sprayed as fine droplets into the polymerization zone. The droplet diameter is preferably within the range 1 to 1000 microns.

Although not usually required, upon completion of polymerization or copolymerization, or when it is desired to terminate polymerization or copolymerization or at least temporarily deactivate the catalyst or catalyst component of this invention, the catalyst can be contacted with water, alcohols, acetone, or other suitable catalyst deactivators a manner known to persons of skill in the art.

A range of polyethylene polymers are considered accessible including high density polyethylene, medium density polyethylene, low density polyethylene, ultra low density polyethylene and elastomeric materials. Particularly important are the polymers having a density in the range of 0.91 to 0.93, grams per cubic centimeter (g/cc) generally referred to in the art as linear low density polyethylene. Such polymers and copolymers are used extensively in the manufacture of flexible blown or cast film.

Depending upon the use of the polymer product, minor amounts of additives are typically incorporated into the polymer formulation such as acid scavengers, antioxidants, stabilizers, and the like. Generally, these additives are incorporated at levels of about 25 to 2000 parts per million by weight (ppm), typically from about 50 to about 1000 ppm, and more typically 400 to 1000 ppm, based on the polymer. In use, polymers or copolymers made according to the invention in the form of a powder are conventionally compounded into pellets. Examples of uses for polymer compositions made according to the invention include use to form fibres, extruded films, tapes, spunbonded webs, molded or thermoformed products, and the like. The polymers may be blown or cast into films, or may be used for making a variety of molded or extruded articles such as pipes, and containers such as bottles or drums. Specific additive packages for each application may be selected as known in the art. Examples of supplemental additives include slip agents, anti-blocks, anti-stats, mould release agents, primary and secondary anti-oxidants, clarifiers, nucleants, uv stabilizers, and the like. Classes of additives are well known in the art and include phosphite antioxidants, hydroxylamine (such as N,N-dialkyl hydroxylamine) and amine oxide (such as dialkyl methyl amine oxide) antioxidants, hindered amine light (uv) stabilizers, phenolic stabilizers, benzofuranone stabilizers, and the like.

Fillers such as silica, glass fibers, talc, and the like, nucleating agents, and colourants also may be added to the polymer compositions as known by the art.

The present invention is illustrated in more detail by the following non-limiting examples.

EXAMPLES

The following abbreviations are used in the examples:
Å=Angstrom units
NMR=nuclear magnetic resonance
Et=ethyl
Bu=butyl
iPr=isopropyl $H_2$=hydrogen
Psi=pounds per square inch
c*=comparative
rpm=revolutions per minute
GC=gas chromatography
FID=Flame Ionization Detector
$R_x$=reaction
Wt=weight
$C_4$'s=butenes
$C_6$'s=hexenes (and 1-$C_6$=hexene-1)
$C_8$'s=octenes (and 1-$C_8$=octene-1)
PE=polyethylene
MAO=Methylalumoxane
Ligand Synthesis
General Experimental Conditions for Ligand Synthesis All reactions involving air and/or moisture sensitive compounds were conducted under nitrogen using standard Schlenk and glovebox techniques. Reaction solvents were purified using the system described by Pangborn et al (Pangborn, A. B. G.; M. A.; Grubbs, R. H.; Rosen, R. K.; Timmers, F. J., Organometallics 1996, 15, 1518 and then stored over activated molecular sieves. Diisopropylamine and 2-bromoanisole were purchased from Aldrich and dried over 4 Å molecular sieves prior to use. 1-Bromo-2-fluoro-benzene, phosphorus trichloride ($PCl_3$), hydrogen chloride gas and n-butyllithium were purchased from Aldrich and used as received. MAO, reported to be 10 wt % Al in toluene, was purchased from Akzo and used as received. Deuterated solvents were purchased from CIL (toluene-$d_8$, THF-$d_8$) and were stored over 4 Å molecular sieves. NMR spectra were recorded on a Bruker 300 MHz spectrometer (300.1 MHz for $^1$H, 121.5 MHz for $^{31}$P, 282.4 for $^{19}$F).

Preparation of $Et_2NPCl_2$ $Et_2NH$ (50.00 mmol, 5.17 mL) was added dropwise to a solution of $PCl_3$ (25.00 mmol, 2.18 mL) in diethyl ether ("ether") (200 mL) at −78° C. After the addition, the cold bath was removed and the slurry was allowed to warm to room temperature over 2 hours. The slurry was filtered and the filtrate was pumped to dryness. The residue was distilled (500 microns, 55° C.) to give the product in quantitative yield.
$^1$H NMR (δ, toluene-$d_8$): 2.66 (doublet of a quartets, 4H, $J_{PH}$=13 Hz, $J_{HH}$=7 Hz), 0.75 (triplet, 6H, J=7 Hz).

Ligand A

Preparation of 2-Methoxyphenyl Lithium

To a solution of 2-bromoanisole (11.2 g, 60.08 mmol) in heptane (150 mL) was slowly added n-BuLi (1.6 M in hexenes, 36.7 mL). White precipitate formed. The slurry was stirred for 0.5 hrs and was filtered. The solid was washed with pentane and was dried under vacuum. The yield was 6.5 g (94%).

Preparation of (2-MeO—$C_6H_4$)$_2$P—N(i-Pr)$_2$

An ether solution (30 mL) of i-$Pr_2NPCl_2$ (0.682 g, 3.375 mmol) was added to 2-methoxyphenyl lithium (2-MeO—$C_6H_4Li$ (0.77 g, 6.75 mmol) in ether (30 mL) at −70° C. The cold bath was removed and the reaction was stirred for 1 hr at room temperature. The solid was filtered off and the filtrate was pumped to dryness. The product was obtained in quantitative yield. $^1$H NMR (toluene-d8, δ): 7.48 (m, 2H), 7.14 (m, 2H), 6.88 (m, 2H), 6.49 (m, 2H), 3.37 (septet, 2H), 3.25 (s, 6H), 1.16 (br s, 12H).

Preparation of (2-MeO—$C_6H_4$)$_2$PCl

HCl (g) was introduced into the head space of a 100 mL Schlenk flask containing a stirred ether solution (30 mL) of (2-MeO—$C_6H_4$)$_2$P—N(i-Pr)$_2$ made in the previous step. A precipitate formed immediately. The pressure of HCl gas was maintained at 4 psi for 0.5 hrs. The slurry was pumped to dryness. The solid was extracted with toluene and the solvent was removed slowly under vacuum. The product crystallized while the solution was evaporated to dryness. The crystalline solid was washed with cold pentane (−70° C.) and was dried under vacuum. The yield was 0.89 g (94%).
$^1$H NMR (toluene-d8, δ): 7.58 (m, 2H), 7.08 (m, 2H), 6.77 (m, 2H), 6.39 (m, 2H), 3.20 (s, 6H).

Preparation of (2-MeO—$C_6H_4$)$_2$P[NH(i-Pr)]

An ether solution (30 ml) of (2-MeO—$C_6H_4$)$_2$PCl (0.45 g, 1.60 mmol) was added slowly to an ether solution (20 mL) of i-$PrNH_2$ (5 mL, 59 mmol) at −70° C. Immediate precipitate was observed. The cold bath was removed and the reaction was stirred at room temperature for 1.5 hrs. The volatiles were removed under vacuum and the solid was extracted with toluene. The toluene solution was pumped to dryness to give the crystalline product in quantitative yield (0.48 g).
$^1$H NMR (toluene-d8, δ): 7.67 (m, 2H), 7.11 (m, 2H), 6.91 (m, 2H), 6.42 (m, 2H), 3.36 (septet, 1H), 3.24 (s, 6H), 2.20 (br.s, 1H), 1.12 (d, 6H, 6.3 Hz).

Preparation of (2-MeO—$C_6H_4$)$_2$P[N(i-Pr)]P(2-F—$C_6H_4$) [Ligand A]

To a slurry of (2-MeO—$C_6H_4$)$_2$P[NH(i-Pr)] (0.498 g, 1.641 mmol) in pentane (25 mL) at −5° C. was added dropwise nBuLi (1.02 mL, 1.6 M in hexene). The white slurry became slightly yellow. After the slurry was vigorously stirred for 40 mins, a pentane solution (20 mL) of (2-F—$C_6H_4$)$_2$PCl (0.466 g, 1.81 mmol) was added. The ice/NaCl bath was removed and the reaction was stirred at room temperature for 2 hrs and pumped to dryness. Dichloromethane (20 mL) was added to the solid. The resulting slurry was stirred for 20 minutes and filtered. The filtrate was pumped to dryness. The residue was soaked with pentane (30 mL) to dissolve the excess of (2-F—$C_6H_4$)$_2$PCl. The pentane supernatant was decanted after standing still at −50° C. for 2 hrs. The process was repeated (solid was re-dissolved in dichloromethane, pumped to dryness, washed with pentane) to afford pure product in almost quantitative yield. The sticky solid crystallized from toluene/heptane at room temperature to give crystalline product (0.40 g).
$^1$H NMR ($CD_2Cl_2$, δ): 7.31 (m, 8H), 7.10 (m, 2H), 6.94 (m, 4H), 6.79 (m, 2H), 3.87 (m, 1H), 3.63 (s, 6H), 1.20 (d, 6H, J=6.6 Hz).
$^{19}$F NMR ($CD_2Cl_2$, δ): −105.41 (br s)
$^{31}$P NMR ($CD_2Cl_2$, δ): 33.24 (br s), 24.61 (br.s)

Ligand B

Preparation of (ortho-F—$C_6H_4$)P($NEt_2$)$_2$

Ortho-F-bromobenzene (5.12 g, 29.23 mmol) in ether (50 mL) was added within 1 hr to n-BuLi (18.27 mL of a 1.6M solution in hexenes) in ether (40 mL) at −85° C. (ethanol/liquid N2 bath). The temperature was maintained between −85° C. to −89° C. during the whole process. The solution was stirred for 2 more hrs at −85° C. to −89° C. The temperature of the cooling bath was lowered to −100° C. and ($Et_2N$)$_2$PCl (6.16 g, 29.23 mmol, prepared from the reaction of $PCl_3$ and four molar equivalents of $Et_2NH$) in 50 mL of ether was added. The reaction was allowed to warm to room temperature within the cold bath overnight and was pumped to dryness. The residue was extracted with pentane. The pentane solution was pumped to dryness to give the product in quantitative yield. GC-MS, $M^+=270$.

Preparation of (ortho-F—$C_6H_4$)$PCl_2$

To the head space of a 250 mL Schlenk flask containing a stirred ether solution (60 mL) of (ortho-F—$C_6H_4$)$P(NEt_2)_2$ prepared in the last step was introduced HCl gas. The pressure of the gas was maintained under 4 Psi during the 0.5 hr reaction time. The volatiles were removed under vacuum and the residue was extracted with pentane (3×50 mL). The filtrate was pumped under gentle vacuum to remove pentane. The remaining liquid was distilled under vacuum (300 microns, 35° C.-40° C. bath temperature) with dry ice cooling the receiver flask to avoid loss. The yield was 5.5 g (96%).

$^1$H NMR ($CD_2Cl_2$, δ): 7.95 (m, 1H), 7.59 (m, 1H), 7.36 (m, 1H), 7.17 (m, 1H)

$^{19}$F NMR ($CD_2Cl_2$, δ): −108.68 (doublet of multiplets, J=81 Hz)

Preparation of (ortho-F—$C_6H_4$)(ortho-MeO—$C_6H_4$)PCl

To a vigorously stirred pentane solution (~180 mL) of (ortho-F—$C_6H_4$)$PCl_2$ (2.132 g, 10.77 mmol) at −70° C. was added dropwise an ether solution (50 mL) of ortho-MeO—$C_6H_4$Li (1.228 g, 10.77 mmol, prepared by a reaction of ortho-MeO—$C_6H_4$Br with n-BuLi in heptane at room temperature). The content became a thick slurry. The reaction was warmed to room temperature in 2.5 hrs. The thick slurry became much thinner. The flask was moved to a glove box and the reaction was stirred at room temperature overnight. The content was filtered and the filtrate was reduced in volume to about 5 mL. The product then began to crystallize and was left to crystallize for 1 hr. The mother liquor was pipetted out and the crystals were washed with cold pentane (−70° C.), then dried under vacuum. The yield was 2.67 g (93%).

$^1$H NMR (THF-$d_8$, δ): 7.61 (m, 1H), 7.42 (m, 2H), 7.28 (m, 1H), 7.10 (m, 3H), 6.98 (m, 1H), 3.73 (s, 3H).

Preparation of (ortho-F—$C_6H_4$)(ortho-MeO—$C_6H_4$)PNH(i-Pr)

i-PrNH2 (2.3 ml) was added to an ether solution (30 mL) of (ortho-F—$C_6H_4$)(ortho-MeO—$C_6H_4$)PCl at room temperature. Immediate precipitate was observed. The slurry was stirred for 1.5 hr and pumped to remove volatiles. The residue was extracted with toluene and filtered. Toluene was removed under vacuum to give an oil which crystallized at −60° C. in a freezer. The yield was quantitative.

$^1$H NMR ($CD_2Cl_2$, δ): 7.49 (m, 1H), 7.41 (m, 1H), 7.32 (m, 1H), 7.26 (m, 1H), 7.11 (m, 1H), 6.99 (m, 1H), 6.93 (m, 1H), 6.82 (m, 1H), 3.65 (s, 3H), 3.29 (m, 1H), 2.28 (br. t, 1H), 1.16 (d, 3H, J=6.6 Hz), 1.15 (d, 3H, J=6.3 Hz).

Preparation of (ortho-F—$C_6H_4$)(ortho-MeO—$C_6H_4$)P[N(i-Pr)]P(ortho-F—$C_6H_4$)$_2$[Ligand B]

n-BuLi (1.38 ml of 1.6M hexenes solution, 2.212 mmol) was added dropwise to a pentane solution (~35 mL) of (ortho-F—$C_6H_4$)(ortho-MeO—$C_6H_4$)PNH(i-Pr) at −7° C. Precipitate was observed almost immediately. The slurry was stirred for 15 minutes. A pentane solution (~30 mL) of (ortho-F—$C_6H_4$)$_2$PCl (0.624 g, 2.43 mmol) was added to the above mentioned slurry. The mixture was stirred at −6° C. for 5 minutes and was stirred at room temperature for 2 hrs. The slurry was pumped to dryness. The solid was extracted with toluene and the toluene solution was pumped to dryness. The residue was re-dissolved in pentane and the pentane solution was allowed to evaporate slowly to give a white crystalline solid (0.62 g). The mother liquor was pumped to dryness to remove toluene completely. The residue crystallized from heptane to give the second crop of product (0.29 g). The combined yield was 0.91 g (80%).

$^1$H NMR ($CD_2Cl_2$, δ): 7.45 (m, 1H), 7.32 (m, 7H), 7.10 (m, 3H), 6.93 (m, 4H), 6.81 (m, 1H), 3.88 (m, 1H), 3.60 (s, 3H), 1.26 (d, 3H, J=6.3 Hz), 1.16 (d, 3H, J=6.3 Hz)

$^{19}$F NMR ($CD_2Cl_2$, δ): −105.46 (br. s, 1F), −105.54 (br.s, 1F), −106.45 (d, J=54 Hz)

Ligand C

Preparation of (ortho-F—$C_6H_4$)(ortho-MeO—$C_6H_4$)P[N(i-Pr)]P(ortho-F—$C_6H_4$)(ortho-MeO-$C_6H_4$ n-BuLi (1.04 mL of a 1.6M hexene solution) was added to pentane solution (30 mL) of (ortho-F—$C_6H_4$)(ortho-MeO—$C_6H_4$)PNH(i-Pr) (0.460 g, 1.67 mmol), which was previously cooled at −60° C. for 15 minutes. Precipitate was observed 1 minute after n-BuLi was added. The slightly yellowish slurry was stirred for 15 minutes at room temperature. Solid (ortho-F—$C_6H_4$)(ortho-MeO—$C_6H_4$)PCl (0.459 g, 1.71 mmol) was then added to the flask. The slurry became white and was left stirring in a glove box for 48 hrs. Volatiles were evaporated under vacuum. The solid was extracted with toluene. The toluene solution was evaporated to about 1 mL and pentane (20 mL) was added. Crystalline solid was collected after 5 hours, washed with cold pentane and dried under vacuum. Pentane (10 mL) was added to the mother liquor. More product crystallized after 16 hours. $^1$H NMR indicated that the two fractions contained two isomers of the title formula in different proportions. The combined yield was 0.45 g (51%).

$^1$H NMR of fraction A ($CD_2Cl_2$, δ): 7.50 (m, 1.5H), 7.30 (m, 5H), 7.19 (m, 1.5H), 7.04 (m, 2H), 6.93 (m, 4H), 6.79 (m, 2H), 3.83 (m, 1H), 3.57 (s, 6H), 1.33 (d, 2.3H, J=6.4 Hz), 1.19 (d, 1.4H, J=5.6 Hz), 1.05 (d, 2.3H, J=6.4 Hz)

$^1$H NMR of fraction B ($CD_2Cl_2$, δ): 7.50 (m, 1H), 7.30 (m, 6H), 7.19 (m, 1H), 7.04 (m, 2H), 6.93 (m, 4H), 6.79 (m, 2H), 3.83 (m, 1H), 3.58 (s, 6H), 1.33 (d, 1.5H, J=6.4 Hz), 1.19 (d, 3H, J=5.6 Hz), 1.05 (d, 1.5H, J=6.4 Hz)

$^{19}$F NMR of combined fractions ($CD_2Cl_2$, δ): −106.1 (br. m), −106.2 (br. m)

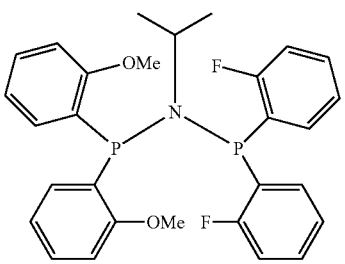

Ligand A

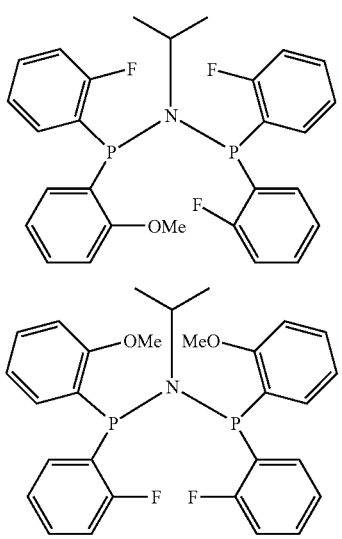

Ligand B

Ligand C

Preparation of (2,3-F$_2$—C$_6$H$_3$)$_2$P—NEt$_2$

To a solution of 1-bromo-2,3-difluorobenzene (5.0 g, 25.9 mmol) in ether (50 mL) was added n-BuLi (17.00 mL of 1.6 M n-BuLi hexene solution, 27.2 mmol) dropwise over 1 hour at −78° C. The reaction was stirred for an additional hour at −78° C. then Et$_2$NPCl$_2$ (2.3 g, 13.0 mmol) in ether (20 mL) was added drop wise over 30 minutes resulting in purple coloured slurry. The reaction was allowed to warm to room temperature overnight. Volatiles were removed in vacuo and the residue was extracted with toluene (3×10 mL) and the solution was pumped to dryness. The product was isolated without further purification yielding a purple oil (4.0 g, 94%).

$^1$H NMR (δ, CD$_2$Cl$_2$): 7.24-7.02 (m, 6H), 3.07 (d of q, 4H, J$_{PH}$=13 Hz, J$_{HH}$=7 Hz), 0.97 (triplet, 6H, J$_{HH}$=7 Hz). $^{19}$F NMR (δ, CD$_2$Cl$_2$): −132.88 (d of m, J=42 Hz), −140.35 (m).

Preparation of (2,3-F—C$_6$H$_3$PCl

A solution of HCl in ether (1.0M, 30.0 mL, 30 mmol) was added rapidly to an ethereal solution (25 mL) of (2,3-F$_2$—C$_6$H$_4$)$_2$P—NEt$_2$ (3.8 g, 11.5 mmol) over a 1 hour period at 0° C. A white precipitate formed immediately and the solution lightened to a yellow colour. The reaction was warmed to room temperature and stirred for an additional 4 hrs at which point slurry was pumped to dryness to remove volatiles. The residue was re-slurried in ether (50 mL), filtered, washed (2×25 mL) and pumped to dryness affording a brown oil (2.96 g, 88%).
Note: Recrystallization from pentane afforded a solid material.

$^1$H NMR (δ, CDCl$_3$): 7.40-7.16 (m, 6H); $^{31}$P NMR (δ, CDCl$_3$): 57.9 (t, J=56 Hz).

Preparation of (2,3-F$_2$—C$_6$H$_3$)$_2$PNH(i-Pr)

To a solution of —PrNH$_2$ (0.5 mL, 5.6 mmol) and NEt$_3$ (2.2 mL, 15.4 mmol) in ether (50 mL) was added an ethereal solution (20 mL) of (2,3-F$_2$—C$_6$H$_4$)PCl (1.00 g, 3.90 mmol) at 0° C. Immediate precipitate was observed. The slurry was stirred for 3 hours, filtered and washed (3×10 mL) with ether. The filtrate was pumped to dryness yielding a brown oil (1.58 g, 98%). $^1$H NMR (δ, CDCl$_3$): 7.29 (m, 2H), 7.11 (m, 4H), 3.36 (septet, 1H, J=7 Hz), 2.26 (brs, 1H), 1.19 (d, 6H, J=7 Hz)]; $^{31}$P NMR (δ, CDCl$_3$): 16.4 (m).

Preparation of (2,3-F$_2$—C$_6$H$_3$)$_2$PN(i-Pr)P(ortho-MeO—C$_6$H$_4$)$_2$

To a solution of (ortho-MeO—C$_6$H$_4$)$_2$PNH(i-Pr) (0.33 g, 1.09 mmol) in pentane (20 mL) maintained at −5° C. was added drop wise a solution of n-BuLi (0.68 mL of 1.6 M n-BuLi hexene solution, 1.09 mmol) leaving a yellow slurry. The mixture was stirred at −5° C. for 15 minutes followed by slow addition an ethereal solution (10 mL) of (2,6-F—C$_6$H$_4$)$_2$PCl (0.32 g, 1.10 mmol). The now white slurry was stirred for 30 minutes at −5° C., and then allowed to slowly warm to room temperature stirring for an additional 3 hours. Volatiles were removed from the solution in vacuo and the residue was extracted into toluene, filtered, washed (3×10 mL) and dried leaving a pale peach pasty solid. The crude product was triturated with pentane to afford a solid, which was recrystallized from heptane at −65° C. yielding a white solid product (0.35 g, 57%).

$^1$H NMR (δ, CD$_2$Cl$_2$): 7.33 (m, 2H), 7.26-7.07 (m, 8H), 6.83 (m, 2H), 6.81 (m, 2H), 3.86 (br. m, 1H), 3.64 (s, 6H), 1.21 (d, J=6 Hz, 6H); $^{19}$F NMR (δ, CD$_2$Cl$_2$): −131.7 (br.)), −140.6 (br.).

Trimerization Reactions

Example 1

A 600-mL reactor fitted with a stirrer (1700 rpm) was purged 3 times with argon while heated at 80° C. The reactor was then cooled to 30° C. and a solution of MAO (5.74 g, 10 wt % MAO in toluene) in 63.26 g of toluene was transferred via a stainless steel cannula to the reactor, followed by 86.7 g of toluene. The reactor was then pressurized with hydrogen (35 psig) and ethylene (35 atmospheres (gauge)) and the temperature adjusted to 45° C. Ligand A (17.58 mg, 0.0357 mmol) in 8.69 g of toluene was added to chromium acetylacetonate (11.52 mg, 0.0329 mmol) in 8.68 g of toluene in a hypovial. The mixture was transferred under ethylene to the pressurized reactor. Immediately after, ethylene was added to increase the reactor pressure to 40 atmospheres (gauge). The reaction was terminated after 27.5 minutes by stopping the flow of ethylene to the reactor and cooling the contents to 30° C., at which point excess ethylene was slowly released from the reactor, cooling the contents to 0° C. The product mixture was transferred to a pre-weighed flask containing approximately 1 g of ethanol and then weighed. The mass of product produced (52.1 g) was taken as the difference in weights before and after the reactor contents were added to the flask with the ethanol. A sample of the liquid product was analyzed by GC-FID. (Example 1, Table 1).

Example 2

A 600-mL reactor fitted with a stirrer (1700 rpm) was purged 3 times with argon while heated at 80° C. The reactor was then cooled to 30° C. and a solution of MAO (5.75 g, 10 wt % MAO in toluene) in 63.25 g of toluene was transferred via a stainless steel cannula to the reactor, followed by 86.7 g of toluene. The reactor was then pressurized with hydrogen (32 psig) and ethylene (35 atmospheres (gauge)) and the temperature adjusted to 55° C. Ligand A (17.52 mg, 0.0356 mmol) in 8.69 g of toluene was added to chromium acetylacetonate (11.59 mg, 0.0332 mmol) in 8.68 g of toluene in a hypovial. The mixture was transferred under ethylene to the pressurized reactor. Immediately after, ethylene was added to increase the reactor pressure to 40 atmospheres (gauge). The reaction was terminated after 16 minutes by stopping the flow of ethylene to the reactor and cooling the contents to 30° C., at which point excess ethylene was slowly released from the reactor, cooling the contents to 0° C. The product mixture was transferred to a pre-weighed flask containing approximately 1 g of ethanol. The mass of product produced (58.2 g) was taken as the difference in weights before and after the reactor contents were added to the flask with the ethanol. A sample of the liquid product was analyzed by GC-FID. (Example 2, Table 1).

Example 3

A 600-mL reactor fitted with a stirrer (1700 rpm) was purged 3 times with argon while heated at 80° C. The reactor was then cooled to 30° C. and a solution of MAO (5.75 g, 10 wt % MAO in toluene) in 63.25 g of toluene was transferred via a stainless steel cannula to the reactor, followed by 86.7 g of toluene. The reactor was then pressurized with hydrogen (29 psig) and ethylene (35 atmospheres (gauge)) and the temperature adjusted to 65° C. Ligand A (17.63 mg, 0.0359 mmol) in 8.69 g of toluene was added to chromium acetylacetonate (11.64 mg, 0.0333 mmol) in 8.68 g of toluene in a hypovial. The mixture was transferred under ethylene to the pressurized reactor. Immediately after, ethylene was added to increase the reactor pressure to 40 atmospheres (gauge). The reaction was terminated after 12.5 minutes by stopping the flow of ethylene to the reactor and cooling the contents to 30° C., at which point excess ethylene was slowly released from the reactor cooling the contents to 0° C. The product mixture was transferred to a pre-weighed flask containing approximately 1 g of ethanol. The mass of product produced (65.7 g) was taken as the difference in weights before and after the reactor contents were added to the flask with the ethanol. A sample of the liquid product was analyzed by GC-FID. (Example 3, Table 1).

Example 4

A 600-mL reactor fitted with a stirrer (1700 rpm) was purged 3 times with argon while heated at 80° C. The reactor was then cooled to 30° C. and a solution of MAO (5.76 g, 10 wt % MAO in toluene) in 63.24 g of toluene was transferred via a stainless steel cannula to the reactor, followed by 86.7 g of toluene. The reactor was then pressurized with hydrogen (17 psig) and ethylene (15 atmospheres (gauge)) and the temperature adjusted to 65° C. Ligand A (17.42 mg, 0.0359 mmol) in 8.69 g of toluene was added to chromium acetylacetonate (11.49 mg, 0.0333 mmol) in 8.68 g of toluene in a hypovial. The mixture was transferred under ethylene to the pressurized reactor. Immediately after, ethylene was added to increase the reactor pressure to 20 atmospheres (gauge). The reaction was terminated after 20 minutes by stopping the flow of ethylene to the reactor and cooling the contents to 30° C., at which point excess ethylene was slowly released from the reactor cooling the contents to 0° C. The product mixture was transferred to a pre-weighed flask containing approximately 1 g of ethanol. The mass of product produced (36.9 g) was taken as the difference in weights before and after the reactor contents were added to the flask with the ethanol. A sample of the liquid product was analyzed by GC-FID. (Example 4, Table 1).

Example 5

A 600-mL reactor fitted with a stirrer (1700 rpm) was purged 3 times with argon while heated at 80° C. The reactor was then cooled to 30° C. and a solution of MAO (5.74 g, 10 wt % MAO in toluene) in 63.26 g of toluene was transferred via a stainless steel cannula to the reactor, followed by 86.7 g of toluene. The reactor was then pressurized with hydrogen (35 psig) and ethylene (35 atmospheres (gauge)) and the temperature adjusted to 75° C. Ligand A (17.47 mg, 0.0355 mmol) in 8.69 g of toluene was added to chromium acetylacetonate (11.54 mg, 0.0330 mmol) in 8.68 g of toluene in a hypovial. The mixture was transferred under ethylene to the pressurized reactor. Immediately after, ethylene was added to increase the reactor pressure to 40 atmospheres (gauge). The reaction was terminated after 11.5 minutes by stopping the flow of ethylene to the reactor and cooling the contents to 30° C., at which point excess ethylene was slowly released from the reactor cooling the contents to 0° C. The product mixture was transferred to a pre-weighed flask containing approximately 1 g of ethanol. The mass of product produced (65.3 g) was taken as the difference in weights before and after the reactor contents were added to the flask with the ethanol. A sample of the liquid product was analyzed by GC-FID. (Example 5, Table 1).

Example 6

A 600-mL reactor fitted with a stirrer (1700 rpm) was purged 3 times with argon while heated at 80° C. The reactor was then cooled to 30° C. and a solution of MAO (5.80 g, 10 wt % MAO in toluene) in 63.20 g of toluene was transferred via a stainless steel cannula to the reactor, followed by 86.7 g of toluene. The reactor was then pressurized with hydrogen (35 psig) and ethylene (35 atmospheres (gauge)) and the temperature adjusted to 45° C. Ligand B (17.23 mg, 0.0355 mmol) in 8.69 g of toluene was added to chromium acetylacetonate (11.65 mg, 0.0334 mmol) in 8.68 g of toluene in a hypovial. The mixture was transferred under ethylene to the pressurized reactor. Immediately after, ethylene was added to increase the reactor pressure to 40 atmospheres (gauge). The reaction was terminated after 9.4 minutes by stopping the flow of ethylene to the reactor and cooling the contents to 30° C., at which point excess ethylene was slowly released from the reactor cooling the contents to 0° C. The product mixture was transferred to a pre-weighed flask containing approximately 1 g of ethanol. The mass of product produced (86.1 g) was taken as the difference in weights before and after the reactor contents were added to the flask with the ethanol. A sample of the liquid product was analyzed by GC-FID. (Example 6, Table 1).

Example 7

A 600-mL reactor fitted with a stirrer (1700 rpm) was purged 3 times with argon while heated at 80° C. The reactor was then cooled to 30° C. and a solution of MAO (3.26 g, 10 wt % MAO in toluene) in 65.74 g of toluene was transferred via a stainless steel cannula to the reactor, followed by 86.7 g of toluene. The reactor was then pressurized with hydrogen (35 psig) and ethylene (35 atmospheres (gauge)) and the temperature adjusted to 45° C. Ligand B (10.05 mg, 0.0197 mmol) in 8.69 g of toluene was added to chromium acetylacetonate (6.48 mg, 0.0186 mmol) in 8.68 g of toluene in a hypovial. The mixture was transferred under ethylene to the pressurized reactor. Immediately after, ethylene was added to increase the reactor pressure to 40 atmospheres (gauge). The reaction was terminated after 16.7 minutes by stopping the flow of ethylene to the reactor and cooling the contents to 30° C., at which point excess ethylene was slowly released from the reactor cooling the contents to 0° C. The product mixture was transferred to a pre-weighed flask containing approximately 1 g of ethanol. The mass of product produced (93.4 g) was taken as the difference in weights before and after the reactor contents were added to the flask with the ethanol. A sample of the liquid product was analyzed by GC-FID. (Example 7, Table 1).

Example 8

A 600-mL reactor fitted with a stirrer (1700 rpm) was purged 3 times with argon while heated at 80° C. The reactor was then cooled to 30° C. and a solution of MAO (3.55 g, 10 wt % MAO in toluene) in 65.45 g of toluene was transferred via a stainless steel cannula to the reactor, followed by 86.7 g of toluene. The reactor was then pressurized with hydrogen (35 psig) and ethylene (35 atmospheres (gauge)) and the temperature adjusted to 75° C. Ligand B (10.49 mg, 0.0205 mmol) in 8.69 g of toluene was added to chromium acetylacetonate (7.13 mg, 0.0204 mmol) in 8.68 g of toluene in a hypovial. The mixture was transferred under ethylene to the pressurized reactor. Immediately after, ethylene was added to increase the reactor pressure to 40 atmospheres (gauge). The reaction was terminated after 11.7 minutes by stopping the flow of ethylene to the reactor and cooling the contents to 30° C., at which point excess ethylene was slowly released from the reactor cooling the contents to 0° C. The product mixture was transferred to a pre-weighed flask containing approximately 1 g of ethanol. The mass of product produced (63.8 g) was taken as the difference in weights before and after the reactor contents were added to the flask with the ethanol. A sample of the liquid product was analyzed by GC-FID. (Example 8, Table 1).

Example 9

A 600-mL reactor fitted with a stirrer (1700 rpm) was purged 3 times with argon while heated at 80° C. The reactor was then cooled to 30° C. and a solution of MAO (5.74 g, 10 wt % MAO in toluene) in 63.26 g of toluene was transferred via a stainless steel cannula to the reactor, followed by 86.7 g of toluene. The reactor was then pressurized with hydrogen (35 psig) and ethylene (35 atmospheres (gauge)) and the temperature adjusted to 45° C. Ligand C (15.54 mg, 0.0296 mmol) in 8.69 g of toluene was added to chromium acetylacetonate (11.64 mg, 0.0333 mmol) in 8.68 g of toluene in a hypovial. The mixture was transferred under ethylene to the pressurized reactor. Immediately after, ethylene was added to increase the reactor pressure to 40 atmospheres (gauge). The reaction was terminated after 15 minutes by stopping the flow of ethylene to the reactor and cooling the contents to 30° C., at which point excess ethylene was slowly released from the reactor cooling the contents to 0° C. The product mixture was transferred to a pre-weighed flask containing approximately 1 g of ethanol. The mass of product produced (64.3 g) was taken as the difference in weights before and after the reactor contents were added to the flask with the ethanol. A sample of the liquid product was analyzed by GC-FID. (Example 9, Table 1).

Example 10

A 600-mL reactor fitted with a stirrer (1700 rpm) was purged 3 times with argon while heated at 80° C. The reactor was then cooled to 30° C. and a solution of MAO (2.88 g, 10 wt % MAO in toluene) in 66.12 g of toluene was transferred via a stainless steel cannula to the reactor, followed by 86.7 g of toluene. The reactor was then pressurized with hydrogen (35 psig) and ethylene (35 atmospheres (gauge)) and the temperature adjusted to 75° C. Ligand C (8.61 mg, 0.0164 mmol) in 8.69 g of toluene was added to chromium acetylacetonate (5.75 mg, 0.0165 mmol) in 8.68 g of toluene in a hypovial. The mixture was transferred under ethylene to the pressurized reactor. Immediately after, ethylene was added to increase the reactor pressure to 40 atmospheres (gauge). The reaction was terminated after 11.04 minutes by stopping the flow of ethylene to the reactor and cooling the contents to 30° C., at which point excess ethylene was slowly released from the reactor cooling the contents to 0° C. The product mixture was transferred to a pre-weighed flask containing approximately 1 g of ethanol. The mass of product produced (65.4 g) was taken as the difference in weights before and after the reactor contents were added to the flask with the ethanol. A sample of the liquid product was analyzed by GC-FID. (Example 10, Table 1).

Example 11

A 600-mL reactor fitted with a stirrer (1700 rpm) was purged 3 times with argon while heated at 80° C. The reactor was then cooled to 30° C. and a solution of MAO (2.90 g, 10 wt % MAO in toluene) in 66.10 g of toluene was transferred via a stainless steel cannula to the reactor, followed by 86.7 g of toluene. The reactor was then pressurized with hydrogen (35 psig) and ethylene (35 atmospheres (gauge)) and the temperature adjusted to 45° C. Ligand C (8.68 mg, 0.0165 mmol) in 8.69 g of toluene was added to chromium acetylacetonate (5.77 mg, 0.0165 mmol) in 8.68 g of toluene in a hypovial. The mixture was transferred under ethylene to the pressurized reactor. Immediately after, ethylene was added to increase the reactor pressure to 40 atmospheres (gauge). The reaction was terminated after 30 minutes by stopping the flow of ethylene to the reactor and cooling the contents to 30° C., at which point excess ethylene was slowly released from the reactor cooling the contents to 0° C. The product mixture was transferred to a pre-weighed flask containing approximately 1 g of ethanol. The mass of product produced (49.7 g) was taken as the difference in weights before and after the reactor contents were added to the flask with the ethanol. A sample of the liquid product was analyzed by GC-FID. (Example 11, Table 1).

Example 12

A 600-mL reactor fitted with a stirrer (1700 rpm) was purged 3 times with argon while heated at 80° C. The reactor was then cooled to 30° C. and a solution of MAO (2.87 g, 10 wt % MAO in toluene) in 66.13 g of toluene was transferred via a stainless steel cannula to the reactor, followed by 86.7 g of toluene. The reactor was then pressurized with hydrogen (20 psig) and ethylene (15 atmospheres (gauge)) and the temperature adjusted to 45° C. Ligand C (8.63 mg, 0.0165 mmol) in 8.69 g of toluene was added to chromium acetylacetonate (5.72 mg, 0.0164 mmol) in 8.68 g of toluene in a hypovial. The mixture was transferred under ethylene to the pressurized reactor. Immediately after, ethylene was added to increase the reactor pressure to 20 atmospheres (gauge). The reaction was terminated after 30 minutes by stopping the flow of ethylene to the reactor and cooling the contents to 30° C., at which point excess ethylene was slowly released from the reactor cooling the contents to 0° C. The product mixture was transferred to a pre-weighed flask containing approximately 1 g of ethanol. The mass of product produced (18.6 g) was taken as the difference in weights before and after the reactor contents were added to the flask with the ethanol. A sample of the liquid product was analyzed by GC-FID. (Example 12, Table 1).

TABLE 1

| Ligand | Example | T° C. | P (bar) | 1-$C_6$ % | total $C_6$'s | 1-$C_8$ % | total $C_8$'s | (1-$C_6$+ 1-$C_8$) % | 1-$C_6$ % | 1-$C_8$ % | Productivity** | $C_4$'s | $C_{10}$ | $C_{12}$ | $C_{12+}$ | PE wt % |
|---|---|---|---|---|---|---|---|---|---|---|---|---|---|---|---|---|
| | | | | \multicolumn{4}{c}{Hexene and Octene Contents in Mixture} | | \multicolumn{2}{c}{Selectivity} | | \multicolumn{5}{c}{Other Products} |
| Ligand A | 1 | 45 | 40 | 68.7 | 68.84 | 24.59 | 24.77 | 93.3 | 99.8 | 99.26 | 66,300 | 2.16 | 1.23 | 0.83 | 2.18 | 0.00 |
| Ligand A | 2 | 55 | 40 | 79.53 | 79.63 | 15.49 | 15.63 | 95.02 | 99.87 | 99.1 | 126,550 | 1.39 | 0.97 | 0.67 | 1.71 | 0.00 |
| Ligand A | 3 | 65 | 40 | 87.24 | 87.31 | 9.01 | 9.12 | 96.32 | 99.92 | 98.79 | 181,960 | 0.8 | 0.71 | 0.51 | 1.55 | 0.30 |
| Ligand A | 4 | 65 | 20 | 85.9 | 85.95 | 7.24 | 7.39 | 93.14 | 99.94 | 97.97 | 64,707 | 1.59 | 1.37 | 1.02 | 2.68 | 0.27 |
| Ligand A | 5 | 75 | 40 | 90.85 | 90.9 | 5.96 | 6.07 | 96.81 | 99.94 | 98.19 | 198,348 | 0.56 | 0.57 | 0.42 | 1.48 | 0.15 |
| Ligand B | 6 | 45-70-55 | 40 | 83.00 | 83.18 | 15.29 | 15.38 | 98.29 | 99.78 | 99.41 | 316,932 | 0.04 | 0.18 | 0.12 | 1.11 | 0 |
| Ligand B | 7 | 45 | 40 | 75.26 | 75.50 | 22.87 | 22.98 | 98.13 | 99.68 | 99.52 | 347,915 | 0.05 | 0.18 | 0.17 | 1.13 | 0 |
| Ligand B | 8 | 75 | 40 | 88.80 | 88.92 | 10.32 | 10.43 | 99.12 | 99.86 | 98.94 | 309,173 | 0.06 | 0.09 | 0.05 | 0.46 | 0 |
| Ligand C | 9 | 45 | 40 | 85.38 | 85.47 | 12.02 | 12.08 | 97.40 | 99.89 | 99.5 | 148,402 | 0.22 | 0.35 | 0.14 | 1.74 | 0 |
| Ligand C | 10 | 75 | 40 | 94.39 | 94.42 | 3.86 | 3.90 | 98.25 | 99.96 | 98.97 | 415,519 | 0.16 | 0.24 | 0.12 | 1.16 | 0 |
| Ligand C | 11 | 45 | 40 | 83.36 | 83.46 | 14.22 | 14.27 | 97.58 | 99.88 | 99.65 | 115,738 | 0.21 | 0.34 | 0.15 | 1.57 | 0 |
| Ligand C | 12 | 45 | 20 | 89.65 | 89.72 | 8.87 | 8.95 | 98.52 | 99.92 | 99.1 | 43,664 | 0.18 | 0.27 | 0.09 | 0.78 | 0 |

**unit in g product/gCr hr
Ligand A iPr—N[P(2-F—C6H4)2][P(2-OMe—C6H4)2]
Ligand B (2-F—Ph)2P—N(iPr)—P(2-OMe—Ph)(2-F—Ph)
Ligand C (2-F—Ph)(2-OMe—Ph)P—N(iPr)—P(2-OMe—Ph)(2-F—Ph)

What is claimed is:

1. A ligand defined by the formula:

wherein each of $Ph_1$, $Ph_2$, $Ph_3$ and $Ph_4$ is a phenyl group bonded to a phosphorus atom, with the provisos that
   i) at least one of $Ph_1$, $Ph_2$, $Ph_3$ and $Ph_4$ is ortho substituted with a halogen selected from the group consisting of fluorine, bromine and chlorine;
   ii) at least one of $Ph_1$, $Ph_2$, $Ph_3$ and $Ph_4$ is ortho substituted with a polar substituent; and
   iii) $R_2$ is selected from the group consisting of hydrogen, $C_{1-20}$ hydrocarbyl and silyl.

2. The ligand of claim 1 wherein said polar substituent is a $C_{1-20}$ alkoxy.

3. The ligand of claim 1 wherein said halogen is fluorine.

4. The ligand of claim 1 wherein $R_2$ is a $C_{1-4}$ hydrocarbyl.

5. The ligand of claim 3 wherein R is isopropyl.

6. A catalyst system comprising:
   a) a transition metal selected from the group consisting of Cr, V, Ti, Ni, and W;
   b) A ligand defined by the formula:

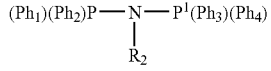

wherein each of $Ph_1$, $Ph_2$, $Ph_3$ and $Ph_4$ is a phenyl group bonded to a phosphorus atom, with the provisos that
   i) at least one of $Ph_1$, $Ph_2$, $Ph_3$ and $Ph_4$ is ortho substituted with a halogen selected from the group consisting of fluorine, bromine and chlorine;
   ii) at least one of $Ph_1$, $Ph_2$, $Ph_3$ and $Ph_4$ is ortho substituted with a polar substituent; and
   iii) $R_2$ is selected from the group consisting of hydrogen, $C_{1-20}$ hydrocarbyl and silyl; and
   c) an activator.

7. A process for the oligomerization of ethylene comprising contacting the catalyst system of claim 6 with ethylene under oligomerization conditions.

8. The process of claim 7 when undertaken at a temperature of from about 10° C. to 300° C. and a pressure of from 5 to 100 atmospheres.

9. The process of claim 7 wherein said transition metal is Cr.

10. The process of claim 7 wherein said activator is methylaluminoxane.

11. The process of claim 7 which is further characterized by producing a liquid product stream which contains from 50 to 90 weight % linear hexenes.

12. The process of claim 11, further characterized in that said linear hexenes contain less than 10 weight % internal hexenes.

* * * * *